(12) United States Patent
Luque et al.

(10) Patent No.: US 12,115,060 B2
(45) Date of Patent: Oct. 15, 2024

(54) ACCOMMODATIVE INTRAOCULAR LENS (71) Applicant: Carl Zeiss Meditec AG, Jena (DE)

(72) Inventors: Sergio Oscar Luque, Vienna (AT); Frank Richter, Potsdam (DE); Jan Buchheister, Jena (DE); Uwe Wolf, Magdala (DE)

(73) Assignee: Carl Zeiss Meditec AG, Jena (DE)

( * ) Notice: Subject to any disclaimer, the term of this patent is extended or adjusted under 35 U.S.C. 154(b) by 792 days.

(21) Appl. No.: 17/163,478

(22) Filed: Jan. 31, 2021

(65) Prior Publication Data

US 2021/0145569 A1    May 20, 2021

Related U.S. Application Data (63) Continuation of application No. PCT/EP2019/069254, filed on Jul. 17, 2019.

(30) Foreign Application Priority Data

Jul. 31, 2018  (DE) ............... 10 2018 212 774.3

(51) Int. Cl.
*A61F 2/16*      (2006.01)
(52) U.S. Cl.
CPC ........ *A61F 2/16* (2013.01); *A61F 2002/1682* (2015.04); *A61F 2002/16901* (2015.04)
(58) Field of Classification Search
CPC ................ A61F 2/16; A61F 2002/1682; A61F 2002/16901; A61F 2/1635; A61F 2/1648; A61F 2002/169; A61F 2/1629; A61F 2/1627; A61F 2002/1681
See application file for complete search history.

(56) References Cited

U.S. PATENT DOCUMENTS 6,197,059 B1    3/2001  Cumming
6,443,985 B1    9/2002  Woods
(Continued)

FOREIGN PATENT DOCUMENTS

AU    2019312759 A1    2/2020
CN    105593743 A      5/2016
(Continued)

OTHER PUBLICATIONS

International Search Report and Written Opinion dated Oct. 30, 2019 of international application PCT/EP2019/069254 on which this application is based and English language translation.
(Continued)

*Primary Examiner* — Jerrah Edwards
*Assistant Examiner* — Jose H. Trevino, III
(74) *Attorney, Agent, or Firm* — Ewers IP Law PLLC; Falk Ewers (57) ABSTRACT

An accommodative intraocular lens for implantation in an eye within a natural capsular bag includes a first lens part with an optical body transparent to light and defining an optical axis, front and rear optical body surfaces, haptics connected permanently to the optical body and designed to come into engagement with the capsular bag, a flexible membrane connected permanently to the haptics or the optical body, the membrane having a center axis which runs congruently or parallel to the optical axis and is transparent to light, and a second lens part with a hollow cylinder which can be positioned with a proximal end on the front membrane surface of the first lens part such that the hollow cylinder and the membrane can be displaced along the optical axis towards the front optical body surface and thus the rear membrane surface undergoes a change in the radius of curvature thereof.

6 Claims, 4 Drawing Sheets

(56) References Cited

U.S. PATENT DOCUMENTS

| | | |
|---|---|---|
| 9,364,316 B1 | 6/2016 | Kahook et al. |
| 9,421,088 B1 | 8/2016 | Kahook et al. |
| 9,987,126 B2 | 6/2018 | Borja et al. |
| 10,478,285 B2 | 11/2019 | Borja et al. |
| 2003/0158560 A1 | 8/2003 | Portney |
| 2007/0100444 A1 | 5/2007 | Brady et al. |
| 2008/0004699 A1 | 1/2008 | Ben Nun |
| 2012/0296424 A1 | 11/2012 | Betser |
| 2014/0180403 A1 | 6/2014 | Silvestrini et al. |
| 2014/0180404 A1 * | 6/2014 | Tran .................. A61F 2/1648 623/6.13 |
| 2016/0157996 A1 | 6/2016 | Dolla et al. |
| 2016/0220350 A1 | 8/2016 | Gerlach |
| 2017/0172732 A1 | 6/2017 | Liu et al. |
| 2021/0145569 A1 | 5/2021 | Sergio et al. |

FOREIGN PATENT DOCUMENTS

| | | | | |
|---|---|---|---|---|
| CN | 107249516 A | 10/2017 | | |
| CN | 107624057 A | 1/2018 | | |
| EP | 0514096 A2 | 11/1992 | | |
| EP | 3829488 B1 | 4/2022 | | |
| WO | WO-2009021326 A1 * | 2/2009 | ........... | A61F 2/1635 |
| WO | WO-2010045305 A1 * | 4/2010 | ........... | A61F 2/1613 |
| WO | 2020025325 A1 | 2/2020 | | |

OTHER PUBLICATIONS

Australian Office Action issued in Australian counterpart application No. AU 2019312759 dated Aug. 10, 2021.
Canadian Office Action issued in Canadian counterpart application No. CA 3,108.107, dated Mar. 30, 2022.
Indian Office Action issued in Indian counterpart application No. IN 202117006502, dated Jan. 13, 2022 and English translation thereof.
Office Action issued in German Patent Application No. DE 10 2018 212 774.3 (from which this application claims priority), dated May 14, 2019 and English language machine translation thereof.
Office Action dated Nov. 28, 2023 issued in Chinese counterpart application No. 2019800564128 and English-language translations thereof.
Search Report dated Nov. 22, 2023 issued in Chinese counterpart application No. 2019800564128 and English-language translations thereof.

* cited by examiner

ACCOMMODATIVE INTRAOCULAR LENS

CROSS REFERENCE TO RELATED APPLICATIONS

This application is a continuation application of international patent application PCT/EP2019/069254, filed Jul. 17, 2019, designating the United States and claiming priority to German application 10 2018 212 774.3, filed Jul. 31, 2018, and the entire content of both applications is incorporated herein by reference.

TECHNICAL FIELD

The disclosure relates to an accommodative intraocular lens.

BACKGROUND

A natural lens of the eye allows objects in the distance and in the vicinity to be seen clearly. This is facilitated by virtue of the lens of the eye being able to alter its form and hence the refractive power. The lens of the eye is contained in a capsular bag which is suspended from zonular fibers which, in turn, are connected to ciliary muscle. When the ciliary muscle relaxes, the zonular fibers tighten, stretching the capsular bag. In the case of a soft lens of the eye, the changing shape of the capsular bag causes the former to also change its shape. As the capsular bag is stretched, the lens of the eye becomes increasingly flattened. This changes the refractive power of the lens of the eye. A flattened lens of the eye leads to a lower refractive power, and so sharp distance vision is possible. This process is reversible, so that when the ciliary muscle is tense, the zonular fibers slacken and the capsular bag is less stretched. Hence, the lens of the eye assumes a shape that is more curved, and so a higher refraction is achieved. This makes it possible to see objects in the vicinity clearly. This variation in the plane of focus is called accommodation.

It is normal for the lens of the eye to lose elasticity with age. The lens of the eye is then less able to change its shape in response to a contraction of the ciliary muscle. This makes it increasingly difficult to focus on close objects. This condition is known as presbyopia. By wearing spectacles or a contact lens, it is possible to compensate the missing refractive power. With increasing age, however, the lens of the eye becomes increasingly inelastic to hard and can also become cloudy. In medicine, such a condition of the lens of the eye is called a cataract. A spectacle lens cannot compensate for the consequences of clouding the lens of the eye, and so it has become common to remove the clouded lens by surgery. To this end, a needle vibrating with ultrasound is inserted into the eye and the hard and cloudy lens of the eye is comminuted into small particles. This process is known as phacoemulsification. Following such phacoemulsification, the particles are aspirated until the capsular bag has been freed from the natural lens of the eye. To facilitate good vision again, an artificial lens of the eye is subsequently implanted in the capsular bag. This artificial lens of the eye is called an intraocular lens.

The artificial lens of the eye is usually a lens with a single focal point (monofocal), and so a patient needs spectacles or a contact lens for clear distance and near vision after an artificial lens of the eye has been implanted. However, there are also thoughts of designing the artificial lens of the eye in such a way that accommodation with a changing plane of focus is possible. Tensing or relaxing a ciliary muscle should make it possible to change the refractive power of the intraocular lens. US 2012/0 296 424 A1 has described such an accommodative intraocular lens. A disadvantage in this case is that such an intraocular lens has a very complex structure and requires a complicated implantation. In addition, the natural capsular bag of each person has a different size, and so such an accommodative intraocular lens is too big or too small for the existing capsular bag for some people and therefore arranged too tightly or too slack in the capsular bag. An accommodative intraocular lens with a simpler structure is disclosed, e.g., in U.S. Pat. No. 6,197,059 B1. The intraocular lens includes an optic body and a haptic coupled thereto, the haptic being so flexible that the optic body can be moved forward or backward along the optical axis of the optic body in response to the movement of the ciliary muscle. However, a disadvantage thereof is that the achievable accommodation is relatively small.

Further accommodative intraocular lenses are disclosed in US 2008/0 004 699 A1 and in U.S. Pat. No. 6,443,985 B1.

SUMMARY

It is an object of the disclosure to provide an accommodative intraocular lens which has a simple structure, which can be implanted with a microincision, which facilitates a large accommodation range, and which can be arranged equally well in a patient with a small capsular bag or large capsular bag.

The object is achieved by the accommodative intraocular lens for implantation in an eye as described herein.

The accommodative intraocular lens for implantation in an eye within a natural capsular bag in the eye, said natural capsular bag being attached at its periphery to a ciliary muscle of the eye with zonular fibers, comprises:

a first lens part comprising:
  a light-transparent optic body with an optical axis, an anterior optic body surface and a posterior optic body surface,
  a haptic securely connected to the optic body, said haptic being configured to engage with the capsular bag in order to arrange the optic body in the middle of the capsular bag,
  a flexible membrane securely connected to the haptic or the optic body, said flexible membrane having an anterior membrane surface and a posterior membrane surface, wherein the membrane is arranged adjacent to the anterior optic body surface, wherein the membrane has a center axis which extends congruent or parallel to the optical axis, wherein the posterior membrane surface has a radius of curvature and wherein the membrane is transparent to light, and a second lens part having a hollow cylinder which can be detachably coupled to the membrane, wherein a proximal end of the hollow cylinder can be placed on the anterior membrane surface of the first lens part such that a compressive force, which acts on a distal end of the hollow cylinder parallel to the optical axis and which is generable by a movement of the ciliary muscle of the eye, renders the hollow cylinder and the membrane displaceable along the optical axis in the direction to the anterior optic body surface and the posterior membrane surface experiences a change in the radius of curvature thereof.

Consequently, the intraocular lens according to an aspect of the disclosure includes a first lens part and a second lens part, the second lens part being detachably couplable to the first lens part. The first lens part includes an optic body and a haptic, as is conventional for every monofocal intraocular lens. The additional membrane is a supplement which can be securely connected to the optic body or the haptic by thermal or chemical action such that the optic body, the haptic and the membrane are formed in one piece. The membrane is relatively easy to produce and takes up little space. Therefore, such a first lens part can be implanted in the eye with a microincision, as is conventional. In this case, a microincision means that a tip of an injector is pushed into a cornea of an eye and the capsular bag arranged therebehind through an opening with a diameter of no more than 3.0 mm, typically less than 2.5 mm and particularly typically less than 1.8 mm, through which the first lens part can be injected into the capsular bag. A microincision is advantageous as this represents only a small injury to the eye, allowing rapid vision recovery following an implant.

The posterior membrane surface has a radius of curvature. In the extreme case, this radius of curvature can be infinite. Then, the posterior membrane surface has the shape of a plane. However, the radius of curvature can also be less than infinity such that the posterior membrane surface adopts a convex or concave form.

The second lens part includes a hollow cylinder which can be detachably coupled to the membrane. An advantage thereof is that the second lens part need not be injected into the capsule bag together with the first lens part. Instead, the second lens part can be injected into the capsular bag at a later time following the implantation of the first lens part. As a hollow cylinder, the second lens part has an even simpler geometry than the first lens part and it can easily be folded or rolled up such that a microincision of the second lens part is possible without problems. A surgeon finds it relatively easy to place the second lens part on the anterior membrane surface of the first lens part. Such a structure of an accommodative intraocular lens is advantageous because the correct height of the second lens part can be determined accurately by measuring the capsular bag prior to surgery for the patient to be treated.

After measuring the eye of the patient, the optic body of the first lens part is accurately adapted to said patient such that the patient can obtain good vision, for example at a distance. Following a measurement of the capsular bag, the second lens part is likewise chosen specifically for the patient to be treated. Consequently, the second lens part does not have a constant height which is the same for every patient. Consequently, the intraocular lens is matched specifically to the patient, not only in view of the optic body and its optical power but also in view of the second lens part.

Following the placement of the proximal end of the hollow cylinder on the anterior membrane surface and the subsequent movement of the ciliary muscle, the capsular bag is stretched or relaxed, as a result of which the shape of the capsular bag changes. Since the distal end of the hollow cylinder is engaged with an interior wall of the capsular bag, a compressive force of different magnitude is exerted on the hollow cylinder and the anterior membrane surface by the change in shape of the capsular bag and so the hollow cylinder and the membrane are displaceable along the optical axis in the direction toward the anterior optic body surface or away therefrom. The different relative position of the membrane in relation to the optic body brings about a change in the radius of curvature of the posterior membrane surface and hence a different refraction, and so accommodation of the eye to objects at a distance or in the vicinity is achievable. The change in the radius of curvature of the posterior membrane surface with increasing displacement of the membrane in the direction of the optic body means a change in the focal point in the direction of di stance vision.

Attention is drawn to the fact that the membrane per se need not cause any refraction and the anterior membrane surface and the posterior membrane surface typically have a plane parallel embodiment with respect to one another. Hence, the membrane can be manufactured very easily. Accommodation is already achieved by virtue of the relative position of the membrane being alterable relative to the optic body and the posterior membrane surface experiencing a change in its radius of curvature in the process. The closer the membrane is displaced to the optic body, the more pronounced is the change in the radius of curvature of the posterior membrane surface.

The first lens part and the second lens part are typically formed from an acrylic polymer. Typically, the first lens part and the second lens part are formed from the same acrylic polymer.

According to an exemplary embodiment of the disclosure, the membrane is coupled to the haptic or the optic body in hermetically sealed fashion such that an interior between the posterior membrane surface and the anterior optic body surface is formed, said interior being filled with a gas. This is advantageous since gas has a different refractive index to an optic body formed from an acrylic polymer material or a membrane. The refractive index of an acrylic polymer is at approximately 1.47 to 1.55 and the refractive index of a gas such as air is at approximately 1.00003, with these values applying at the wavelength of 589 nm of the sodium D-line. Consequently, a refractive index difference of approximately 0.5 can be achieved by using a gas in the interior. If the height of the interior alters due to a displacement of the hollow cylinder and the membrane relative to the optic body such that there is a change in the gas volume present between the posterior membrane surface of the anterior optic body surface, this has a change in the refractive power of the entire intraocular lens as a consequence. A relatively large change in refraction can already be achieved by a small accommodation and hence displacement of hollow cylinder and membrane relative to the optic body and thus change in the radius of curvature of the posterior membrane surface.

According to an exemplary embodiment of the disclosure, the gas-filled volume in the interior is restricted to a volume in the range of 3 to 10 mm$^3$, typically 4 to 6 mm$^3$. This is advantageous that an expansion of the gas only leads to a small displacement of the membrane in relation to the optic body and hence a small change in the radius of curvature of the posterior membrane surface even in the case of atmospheric pressure in the surroundings of the patient that deviates from the otherwise usual atmospheric pressure for the patient, for example during a stay in the mountains or in an airplane.

Typically, the membrane has guide elements, with which the hollow cylinder can engage and consequently be able to be placed on the membrane centrally with respect to the optical axis. This is advantageous since the hollow cylinder can consequently be arranged optimally in relation to the membrane, as a result of which an optimal function of the intraocular lens can be ensured. A permanently stable relative position of the hollow cylinder in relation to the membrane can be achieved by the guide elements.

According to an exemplary embodiment of the disclosure, the membrane has a central region and a peripheral region, the central region having a larger thickness than the peripheral region. As a result, the peripheral region adopts the function of a film hinge and it is possible to reliably change the radius of curvature of the posterior membrane surface using little force.

Moreover, it is possible that the membrane is displaceable in such a way that the posterior membrane surface can be brought into contact with at least one apex of the anterior optic body surface. Hence, there is a first state in which the membrane is not in contact with the anterior optic body surface and a second state in which the membrane is in contact with the anterior optic body surface. This is advantageous since a significant difference in the refraction of the overall intraocular lens can be achieved in this way. There is a significant change in the refraction when the membrane comes into contact not only with the apex but also with a closed region of the anterior optic body surface as a result of an increasing compressive force on the distal end of the hollow cylinder.

Typically, the hollow cylinder has a circumferential collar at the distal end, it being possible to bring said collar into engagement with an interior wall of the capsular bag. This achieves larger surface contact with the interior wall of the capsular bag. This is advantageous since this facilitates a very stable relative position of the hollow cylinder in the capsular bag.

According to an exemplary embodiment of the disclosure, an elevation with a height of more than 0.05 mm is formed on the anterior optic body surface. The elevation can have the shape of a hemisphere, a ring or a ring segment. If this elevation has a height larger than 0.05 mm, surface contact between the posterior membrane surface and the anterior optic body surface can be prevented in the case of a displacement of the membrane in the direction of the anterior optic body surface and a change in the radius of curvature of the posterior membrane surface accompanying this. If the posterior membrane surface and the anterior optic body surface each only have little roughness, the elevation can prevent large-area adhesion, for example through adhesion of the two surfaces to one another

BRIEF DESCRIPTION OF THE DRAWINGS

The disclosure will now be described with reference to the drawings wherein.

DESCRIPTION OF EXEMPLARY EMBODIMENTS

Figure 1:
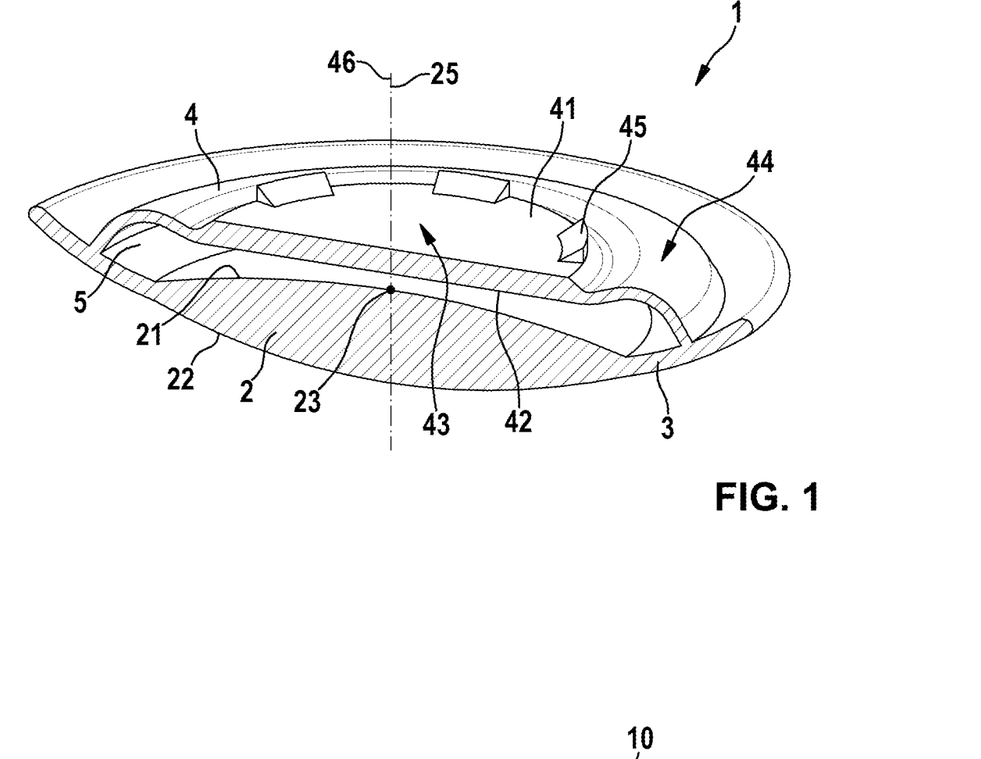
FIG. 1 shows a schematic perspective cross-sectional illustration of a first lens part of the intraocular lens according to an exemplary embodiment of the disclosure.
Figure 3:
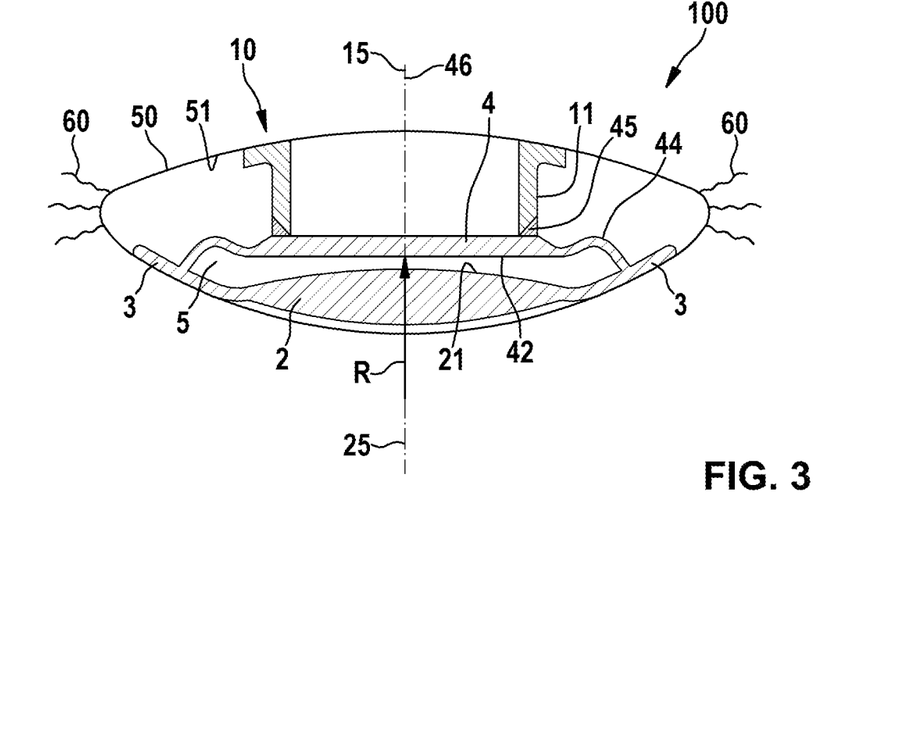
FIG. 3 shows a schematic cross-sectional illustration of the intraocular lens in a capsular bag of an eye when the zonular fibers are not stretched according to a first exemplary embodiment of the disclosure.

FIG. 1 illustrates a schematic perspective cross-sectional illustration of a first lens part 1 of the intraocular lens 100 shown in FIG. 3 according to an exemplary embodiment of the disclosure. The first lens part 1 has an optic body 2 transparent to light, with an anterior optic body surface 21 and a posterior optic body surface 22. In this exemplary embodiment, the optic body 2 has an embodiment that is rotationally symmetric about an optical axis 25. A haptic 3 is securely connected to and embodied in one piece with the optic body 2. The haptic 3 is set up to come into engagement with a capsular bag 50 in order to arrange the optic body 2 in the middle of the capsular bag 50; see FIG. 3.

A flexible membrane 4 is securely connected to the haptic 3 or the optic body 2, the membrane 4 being embodied in one piece with the haptic 3 in the exemplary embodiment shown in FIG. 1. The membrane 4 has an anterior membrane surface 41 and a posterior membrane surface 42 and is arranged adjacent to the anterior optic body surface 21. The membrane 4 has a center axis 46 which extends congruently to the optical axis 25 of the optic body 2 in this exemplary embodiment, the membrane 4 being formed from a light-transparent material. The membrane 4 has a central region 43 and a peripheral region 44, the central region 43 having a larger thickness than the peripheral region 44. The anterior membrane surface 41 and the posterior membrane surface 42 are embodied in plane-parallel fashion to one another in the central region 43. The peripheral region 44 of the membrane 4 is connected to the haptic in ring-shaped fashion and embodied in arched fashion, as a result of which it forms an upper segment of a torus. This facilitates a displacement of the central region 43 along the center axis 46 of the membrane 4. In such an embodiment, the peripheral region 44 of the membrane 4 has a resilient property in the case of the movement of the membrane 4 along the center axis 46. The anterior membrane surface 41 is provided with guide elements 45, which can come into engagement with the second lens part 10.

Figure 2:
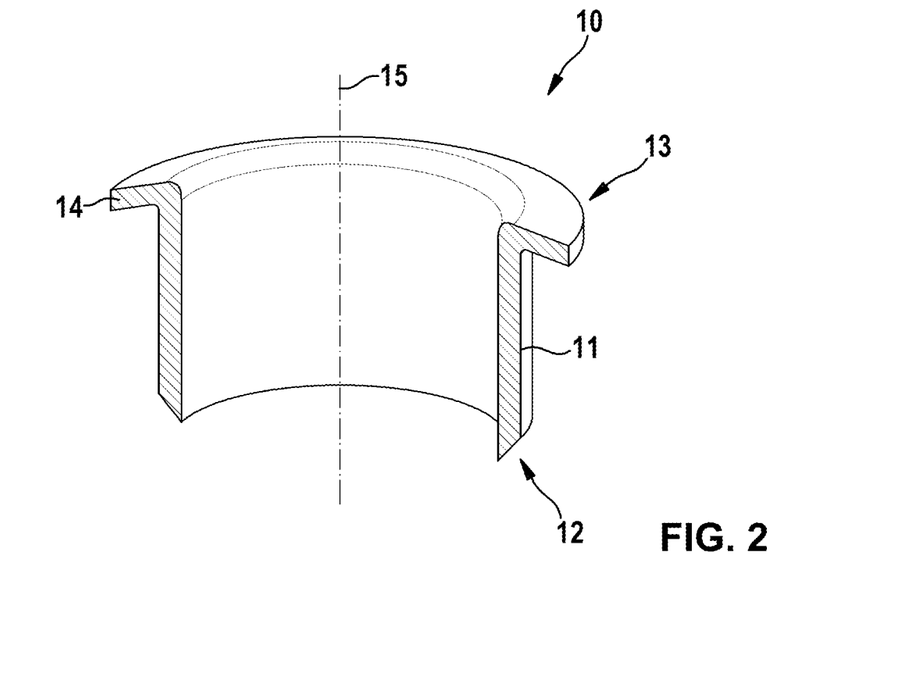
FIG. 2 shows a schematic perspective cross-sectional illustration of a second lens part of the intraocular lens according to an exemplary embodiment of the disclosure.

The second lens part 10 has a hollow cylinder 11 which has a rotationally symmetric embodiment about a center axis 15; see FIG. 2. The hollow cylinder 11 is provided with a proximal end 12, which can come into interlocking engagement with the guide elements 45 of the membrane 4 of the first lens part 1. A circumferential collar 14 is provided at the opposite distal end 13 of the hollow cylinder 11.

When the first lens part 1 is implanted in a capsular bag 50 of an eye, see FIG. 3, then the second lens part 10 can subsequently be implanted in the capsular bag. The haptic 3 is embodied in such a way that it touches an interior wall 51 of the capsular bag 50 and hence aligns the optic body 2 in the capsular bag 50 in such a way that the optical axis 25 of the optic body 2 extends substantially congruently with the center axis of the capsular bag 50. Then, the second lens part 10 can be placed on the anterior membrane surface 41 in such a way that the center axis 15 of the hollow cylinder 10 extends congruently with the optical axis 25 of the optic body. The collar 14 of the hollow cylinder 11 rests against the inner wall 51 of the capsular bag 50 and transfers a compressive force F, cf. FIG. 4, on the membrane 4 when zonular fibers 60 of the eye are tensioned and the capsular bag 50 is flattened in terms of its cross-sectional form thereby.

Figure 4:
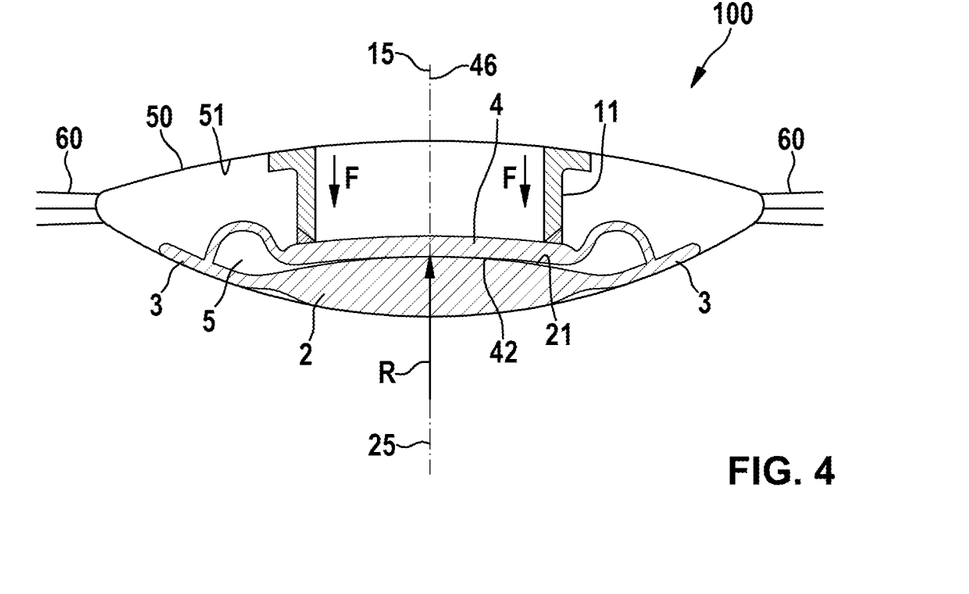
FIG. 4 shows a schematic cross-sectional illustration of the intraocular lens as shown in FIG. 3, in a capsular bag of an eye when the zonular fibers are stretched.

FIG. 3 shows the capsular bag 50 in a state in which the zonular fibers are slack and hence the cross-sectional form of the capsular bag 50 has a relatively convex embodiment. Near-region focusing can be achieved in this state. FIG. 4 shows the capsular bag in a state in which the zonular fibers 60 are tensioned such that a compressive force F parallel to the optical axis 25 acts on the collar 14 at the distal end 13 of the hollow cylinder 11, said compressive force displacing the hollow cylinder 11 and the membrane 4 in the direction of the anterior optic body surface 21. Distance-region focusing can be achieved as a result.

In the interior 5, there is quite a lot of gas between the posterior membrane surface 42 and the anterior optic body surface 21 in the exemplary embodiment illustrated in FIG. 3. In the case of accommodation and a correspondingly flattened capsular bag 50 as shown in FIG. 4, the gas is displaced under the peripheral region 44 of the membrane 4 such that only very little gas, or no gas at all, is present between the posterior membrane surface 42 and the anterior optic body surface 21. This brings about a significant change in the refraction, which is assisted by the deformation of the membrane 4 and a partly planar contact between the posterior membrane surface 42 and the anterior optic body surface 21.

Further, a radius of curvature R, which indicates the radius of curvature of the posterior membrane surface 42, is plotted in FIG. 3. In the exemplary embodiment shown in FIG. 3, the radius of curvature R is infinite since the posterior membrane surface 42 forms a flat area. In the state shown in FIG. 4, in which the membrane has relatively pronounced arching and in part rests against the anterior optic body surface 21 in planar fashion, the radius of curvature is less than infinity. In the case of planar contact between the posterior membrane surface 42 and the anterior optic body surface 21, the radius of curvature of the posterior membrane surface 42 is consequently identical to a radius of curvature of the anterior optic body surface 21.

Figure 5:
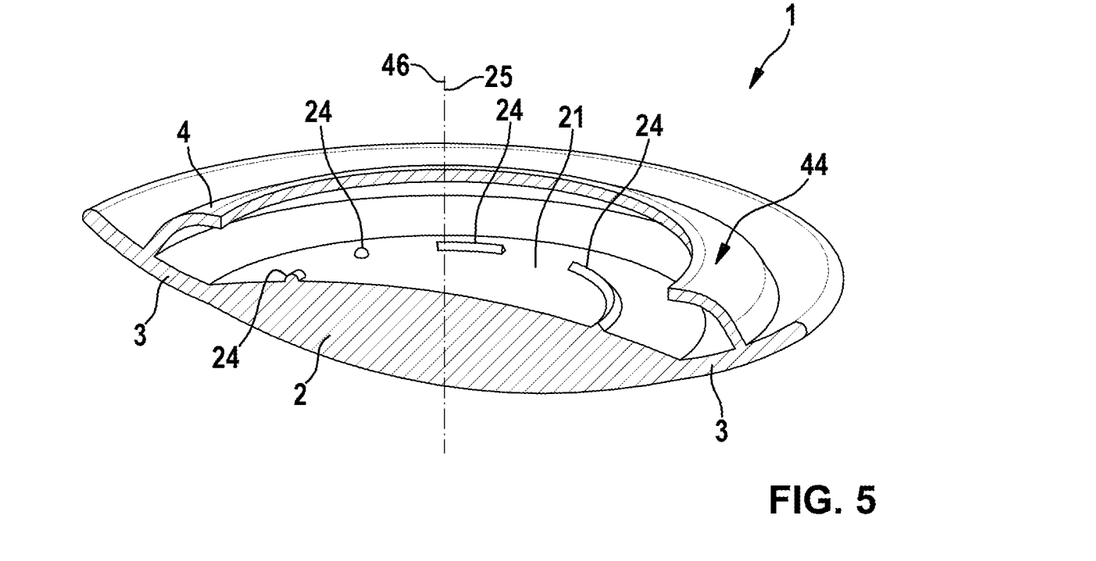
FIG. 5 shows a schematic perspective cross-sectional illustration of the first lens part of the intraocular lens with elevations on a surface of an optic body according to a further exemplary embodiment of the disclosure.
Figure 6:
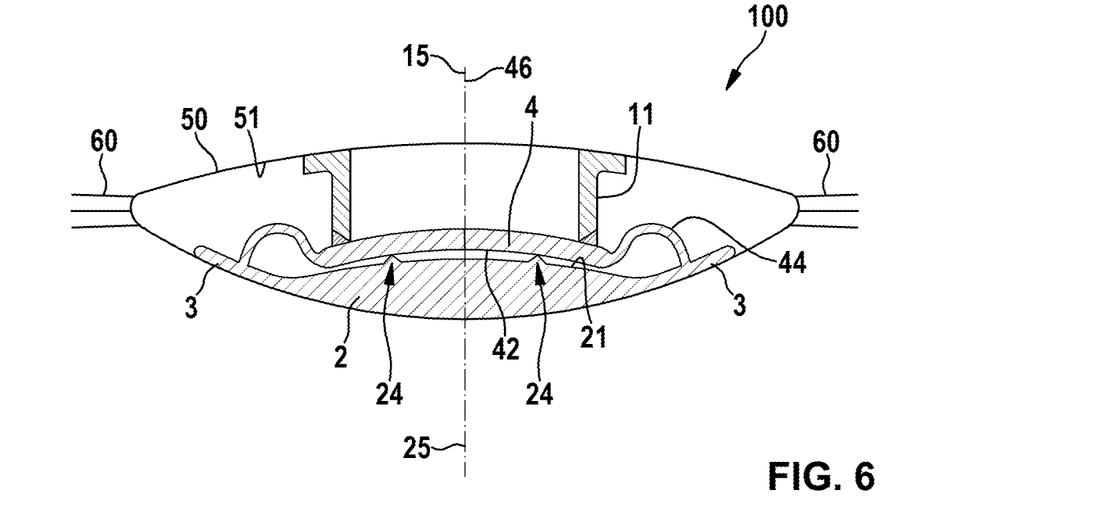
FIG. 6 shows a schematic cross-sectional illustration of the intraocular lens shown in FIG. 5, in a capsular bag of an eye when the zonular fibers are stretched.

FIG. 5 illustrates a schematic perspective cross-sectional illustration of a further exemplary embodiment of the first lens part of the intraocular lens according to the disclosure. The anterior optic body surface 21 is provided with elevations 24. By way of example, an elevation 24 can have the form of a hemisphere or a ring segment or a completely closed ring. As a result, large-area contact and, consequently, possible adhesion between the posterior membrane surface 42 and the anterior optic body surface 21 can be avoided in the case of a relatively large displacement of the membrane 4 in the direction of the optic body 2. Thus, the elevations 24 form a bearing which only allows a punctiform or line contact between the posterior membrane surface 42 and the anterior optic body surface 21; cf. FIG. 6.

Figure 7:
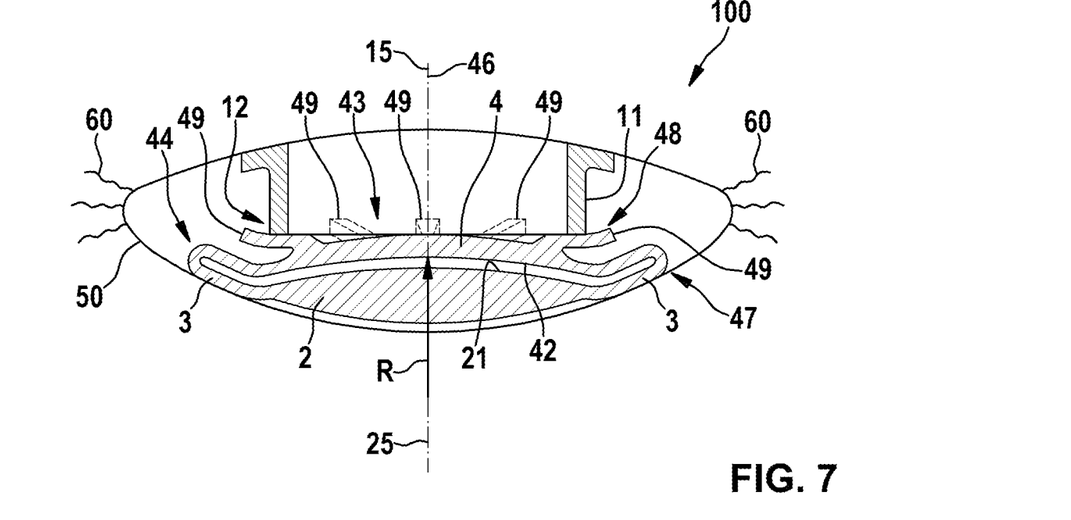
FIG. 7 shows a schematic cross-sectional illustration of the intraocular lens in a capsular bag of an eye when the zonular fibers are not stretched according to yet another exemplary embodiment of the disclosure.

FIG. 7 illustrates a further exemplary embodiment of the disclosure in a cross-sectional view. The membrane 4 has a central region 43 and a peripheral region 44. The haptic 3 and the peripheral region 44 of the membrane are not only made in one piece but are also interconnected in the cross section along a curved line 47 which has a U-shaped embodiment in the cross section. However, it is also possible for the peripheral region 44 of the membrane 4 to be directly connected to the haptic 3 or the optic body 2, in particular the anterior optic body surface 21, without an embodiment that is U-shaped in cross section. Provided along an outer edge 48 of the central region 43 of the membrane 4 in a manner directed radially to the outside are a plurality of bending elements 49 in the form of a bending bar fixed at one side. Typically, the bending elements 49 are arranged at the same horizontal angle or azimuth with respect to one another. The hollow cylinder 11 is embodied in such a way that the proximal end 12 thereof can sit on the bending elements 49.

Figure 8:
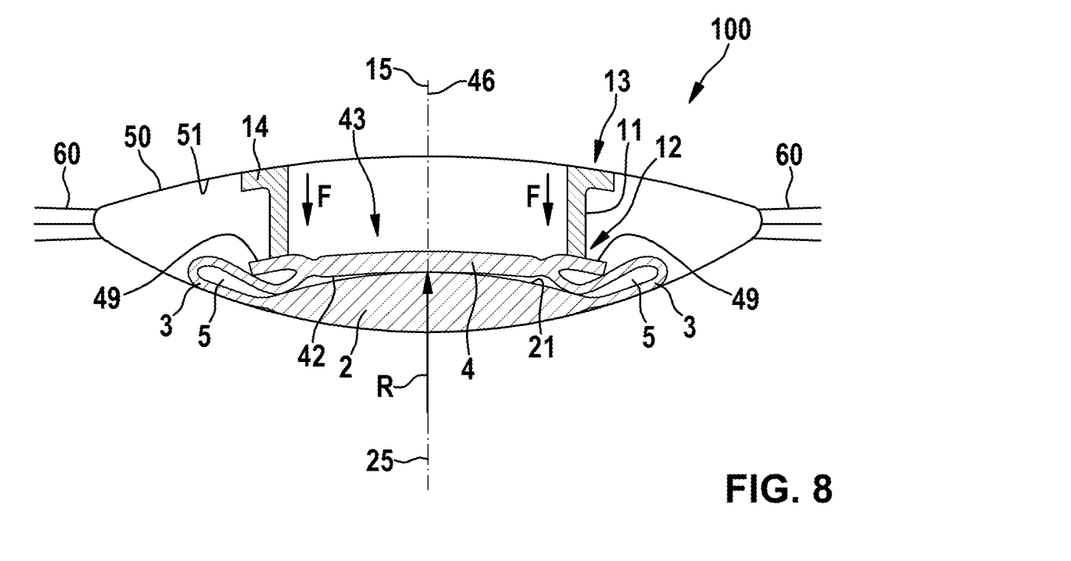
FIG. 8 shows a schematic cross-sectional illustration of the intraocular lens shown in FIG. 7, in a capsular bag of an eye when the zonular fibers are stretched.

If the zonular fibers 60 are slack and the cross-sectional form of the capsular bag 50 is relatively convex, the posterior membrane surface 42 has a maximum radius R that is significantly smaller than infinity; cf. FIG. 7. In the slack state of the zonular fibers 60, the proximal end 12 of the hollow cylinder 11 is only seated on the bending elements 49 without causing significant bending of the bending elements 49 or the membrane 4. If the zonular fibers 60 are tensioned, cf. FIG. 8, such that a compressive force F parallel to the optical axis 25 acts in the direction toward the optic body 2 on the collar 14 at the distal end 13 of the hollow cylinder 11, the hollow cylinder 11, with its proximal end 12, deforms the bending elements 49 in the direction of the peripheral region 44 of the membrane 4. This causes the central region 43 of the membrane 4 to experience less arching and be flattened. The radius R of the posterior membrane surface 42 increases as a result, with this typically being implemented at a membrane zone which is close to the center axis 46 of the membrane 4. The maximum radius R of the posterior membrane surface 42 can be infinite in such a membrane zone. As a consequence, the refractive power of the intraocular lens 100 reduces and distance focusing is achieved. This effect can be amplified by virtue of a fluid such as, e.g., an oil, typically silicone oil, a gel, typically a silicone gel with a Shore-hardness ranging from 1 (durometer type OOO) to 100 (durometer type OO), or a gas being contained in a region between the posterior membrane surface 42 and the anterior optic body surface 21. By moving the hollow cylinder 11 in the direction of the optic body 2, this fluid can be displaced in the direction of the interior 5 such that relatively little fluid is present in the central region 43 between the posterior membrane surface 42 and the optic body surface 21. This causes an additional change in the refraction of the intraocular lens 100.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 First lens part
2 Optic body
3 Haptic
4 Membrane
5 Interior
10 Second lens part
11 Hollow cylinder
12 Proximal end of the hollow cylinder
13 Distal end of the hollow cylinder
14 Collar
15 Center axis of the hollow cylinder
21 Anterior optic body surface
22 Posterior optic body surface
23 Apex of the anterior optic body surface
24 Elevation
25 Optical axis of the optic body
41 Anterior membrane surface
42 Posterior membrane surface
43 Central region of the membrane 44 Peripheral region of the membrane
45 Guide element
46 Center axis of the membrane
47 Curved line
48 Outer edge of the central region of the membrane
49 Bending element
50 Capsular bag
51 Interior wall of the capsular bag
60 Zonular fibers
100 Accommodative intraocular lens
F Compressive force
R Radius of curvature of the posterior membrane surface

What is claimed is:

1. An accommodative intraocular lens for implantation in an eye within a natural capsular bag in the eye, said natural capsular bag being attached at its periphery to a ciliary muscle of the eye with zonular fibers, the accommodative intraocular lens comprising:
   a first lens part comprising:
      a light-transparent optic body with an optical axis, an anterior optic body surface and a posterior optic body surface,
      a haptic securely connected to the light-transparent optic body, said haptic being configured to engage with the natural capsular bag to arrange the light-transparent optic body in a middle of the natural capsular bag, and
      a flexible membrane securely connected to the haptic or the light-transparent optic body, said flexible membrane having an anterior membrane surface and a posterior membrane surface, the flexible membrane being arranged adjacent to the anterior optic body surface, the flexible membrane defining a center axis which extends congruent or parallel to the optical axis, the posterior membrane surface having a radius of curvature, and the flexible membrane being transparent to light; and
   a second lens part having a hollow cylinder which can be detachably coupled to the flexible membrane, wherein a proximal end of the hollow cylinder can be placed on the anterior membrane surface of the first lens part such that a compressive force, which acts on a distal end of the hollow cylinder parallel to the optical axis and which is generable by a movement of the ciliary muscle of the eye, renders the hollow cylinder and the flexible membrane displaceable along the optical axis in a direction to the anterior optic body surface and the posterior membrane surface experiences a change in the radius of curvature thereof,
   wherein the flexible membrane has a central region and a peripheral region and is coupled to the haptic or the light-transparent optic body in hermetically sealed fashion such that an interior between the posterior membrane surface and the anterior optic body surface is formed,
   wherein the interior is filled with a gas, and
   wherein the flexible membrane is configured such that the gas is displaced under the peripheral region in an accommodated state of the intraocular lens.

2. The accommodative intraocular lens as claimed in claim 1, wherein the flexible membrane has guide elements, with which the hollow cylinder can engage such that the flexible membrane can be placed on the flexible membrane centrally with respect to the optical axis.

3. The accommodative intraocular lens as claimed in claim 1, wherein the flexible membrane has a central region and a peripheral region, and
   wherein the central region has a larger thickness than the peripheral region.

4. The accommodative intraocular lens as claimed in claim 1, wherein the flexible membrane is displaceable such that the posterior membrane surface can be brought into contact with at least one apex of the anterior optic body surface.

5. The accommodative intraocular lens as claimed in claim 1, wherein the hollow cylinder has a circumferential collar at the distal end, and
   wherein the circumferential collar can be brought into engagement with an interior wall of the natural capsular bag.

6. The accommodative intraocular lens as claimed in claim 1, wherein an elevation with a height of more than 0.05 mm is formed on the anterior optic body surface.

* * * * *